(12) United States Patent
Weibel et al.

(10) Patent No.: US 7,439,248 B1
(45) Date of Patent: *Oct. 21, 2008

(54) PHARMACEUTICAL COMPOSITION AND THE PROCESS FOR ITS PREPARATION

(75) Inventors: Helle Weibel, Hillerød (DK); Thyge Borup Hjorth, Farum (DK)

(73) Assignees: Dr. Reddy's Laboratories Limited, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/450,609

(22) Filed: Nov. 30, 1999

Related U.S. Application Data

(60) Provisional application No. 60/112,248, filed on Dec. 14, 1998.

(30) Foreign Application Priority Data

Dec. 1, 1998 (DK) .............................. 1998 01580

(51) Int. Cl.
*A61K 31/517* (2006.01)
*A61K 31/425* (2006.01)

(52) U.S. Cl. ................ 514/266.1; 514/256; 514/258.1; 514/365; 514/369

(58) Field of Classification Search ................ 514/259, 514/250, 257, 266.1, 256, 258.1, 365, 369
See application file for complete search history.

(56) References Cited

U.S. PATENT DOCUMENTS

| | | | | |
|---|---|---|---|---|
| 4,280,997 A | * | 7/1981 | Van Leverink | 424/676 |
| 5,532,256 A | | 7/1996 | Malamas et al. | 514/361 |
| 5,972,970 A | * | 10/1999 | Sohda et al. | 514/340 |
| 6,710,050 B2 | * | 3/2004 | Weibel et al. | 514/266.2 |
| 6,866,867 B2 | * | 3/2005 | Staniforth et al. | 424/499 |

FOREIGN PATENT DOCUMENTS

| | | |
|---|---|---|
| EP | 0 945 134 | 9/1999 |
| WO | WO 92/17161 | 10/1992 |
| WO | WO 95/06461 | 3/1995 |
| WO | WO 96/18386 | 6/1996 |
| WO | WO 97/41097 | 11/1997 |
| WO | WO 98/45291 | 10/1998 |
| WO | WO 2006002255 A2 | 6/2005 |
| WO | WO 2006002255 A3 | 6/2005 |

* cited by examiner

*Primary Examiner*—Jennifer Kim
(74) *Attorney, Agent, or Firm*—Dority & Manning, P.A.

(57) ABSTRACT

The present invention provides a new stable pharmaceutical composition containing 5-[[4-[3-Methyl-4-oxo-3,4-dihydro-2-quinazolinyl]methoxy]phenyl-methyl]thiadiazolidine-2,4-dione as active ingredient.

2 Claims, No Drawings

PHARMACEUTICAL COMPOSITION AND THE PROCESS FOR ITS PREPARATION

CROSS-REFERENCE TO RELATED APPLICATIONS

This application claims priority under 35 U.S.C. 119 of Danish application PA 1998 01580 filed Dec. 1, 1998 and of U.S. Provisional application 60/112,248 filed Dec. 14, 1998, the contents of which are fully incorporated herein by reference.

The subject-matter of the present invention is a new pharmaceutical composition containing 5-[[4-[3-Methyl-4-oxo-3,4-dihydro-2-quinazolinyl]methoxy]phenyl-methyl]thiadiazolidine-2,4-dione as active ingredient and the process for its preparation.

5-[[4-[3-Methyl-4-oxo-3,4-dihydro-2-quinazolinyl]methoxy]phenyl-methyl]thiadiazolidine-2,4-dione and pharmaceutically acceptable salts thereof has been found useful in the treatment of type 2 diabetes acting as a insulin sensitizer as disclosed in PCT Publication WO 97/41097.

The active ingredient is present as the base or as a pharmaceutically acceptable salt, preferably as the potassium salt.

Various solutions have been proposed for the preparation of medications based on 5-[[4-[3-Methyl-4-oxo-3,4-dihydro-2-quinazolinyl]methoxy]phenyl-methyl]thiadiazolidine-2,4-dione.

The aim of the present invention is to provide a new composition intended for the preparation of 5-[[4-[3-Methyl-4-oxo-3,4-dihydro-2-quinazolinyl]methoxy]phenyl-methyl]thiadiazolidine-2,4-dione with improved stability, in particular solid dosage forms thereof.

It has been found in fact that 5-[[4-[3-Methyl-4-oxo-3,4-dihydro-2-quinazolinyl]meth-oxy]-phenyl-methyl]thiadiazolidine-2,4-dione and its pharmaceutically acceptable salts may decompose in the presence of and in contact with water. Further it has been observed that decomposing may occur in the presence of oxygen.

Thus, from a first aspect, the subject-matter of the present invention is a pharmaceutical composition intended for the preparation of dosage forms and in particular solid dosage forms containing an efficacious quantity of 5-[[4-[3-Methyl-4-oxo-3,4-dihydro-2-quinazolinyl]methoxy]phenyl-methyl]thiadiazolidine-2,4-dione or of one of its pharmaceutically acceptable salts as active ingredient.

The present invention is based on the surprising discovery of the fact that the stability of 5-[[4-[3-Methyl-4-oxo-3,4-dihydro-2-quinazolinyl]methoxy]phenyl-methyl]thiadiazolidine-2,4-dione, or of one of its pharmaceutically acceptable salts, can be considerably improved in preparations containing 5-[[4-[3-Methyl-4-oxo-3,4-dihydro-2-quinazolinyl]methoxy]phenyl-methyl]thiadiazolidine-2,4-dione or of its pharmaceutically acceptable salts and antioxidant agent if the product is composed of excipients which do not contain water.

Pharmaceutically acceptable salts forming part of this invention include salts such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, aluminium salts. Salts may include acid addition salts where appropriate which are, sulphates, nitrates, phosphates, perchlorates, borates, hydrohalides, acetates, tartrates, maleates, citrates, succinates, palmoates, methane-sulplionates, benzoates, salicylates, hydroxynaphthoates, benzenesulfonates, ascorbates, glycerophosphates, ketoglutarates and the like.

5-[[4-[3-Methyl-4-oxo-3,4-dihydro-2-quinazolinyl]methoxy]phenyl-methyl]thiadiazolidine-2,4-dione, together with a conventional adjuvant, antioxidant carrier, or diluent, and if desired a pharmaceutically acceptable acid addition salt thereof, may be placed into the form of pharmaceutical compositions and unit dosages thereof, and in such form may be employed as solids, such as tablets or filled capsules, or oral powders to be diluted immediately before use filled with the same, all for oral use, in the form of suppositories for rectal administration; or as pessaries for vaginal use; or in the form of sterile injectable powders for parenteral, transdermal, nasal, pulmonary and ocular use.

Within the framework of the present description and of the claims, by powders is meant any mixture of components, granulated or not, intended to be placed in solution and/or in suspension in water, or again to be ingested directly or by any other appropriate means as for example in a mixture with a food product.

In accordance with a particular characteristic of the invention, the manufacture of tablets are carried out as a direct compression.

In accordance with another particular characteristic, this composition also contains pharmaceutically acceptable excipients.

In accordance with a particular characteristic of the invention, the antioxidant agent cited above is selected from among α-tocopherol, γ-tocopherol, δ-tocopherol, extracts of natural origin rich in tocopherol, L-ascorbic acid and its sodium or calcium salts, ascorbyl palmitate, propyl gallate (PG), octyl gallate, dodecyl gallate, butylated hydroxy anisole (BHA) and butylated hydroxy toluene (BHT).

In accordance with a currently preferred embodiment, the antioxidant agent will be α-tocopherol.

In accordance with another particular characteristic of the invention, the diluent is lactose and/or cellulose microcrystalline, magnesium stearate, talc.

However, any other pharmaceutically acceptable diluents could be used if the diluents has a low water content.

The quantities of diluents can be easily determined by a person skilled in the art and depend of course on the final pharmaceutical form required.

Generally speaking, a composition which complies with the present invention and which are intended for the preparation of tablets, may contain, expressed in parts by weight per 100 parts of 5-[[4-[3-Methyl-4-oxo-3,4-dihydro-2-quinazolinyl]methoxy]phenyl-methyl]thiadiazolidine-2,4-dione, or of one of its pharmaceutically acceptable salts:

between 100 and 400,000 parts by weight of anhydrous lactose;

between 1 and 100 parts by weight of an antioxidant;

between 50 and 500 parts by weight of pregelatinized starch;

between 1000 and 10,000 parts by weight of microcrystalline cellulose;

between 10 and 500 parts by weight of crospovidone;

between 10 and 500 parts by weight of silicon dioxide;

between 10 and 500 parts by weight of hydrogenated vegetable oil;

between 10 and 500 parts by weight of magnesium stearate;

between 10 and 500 parts by weight of hydroxypropyl methylcellulose;

between 10 and 500 parts by weight of hydroxypropyl cellulose;

between 1000 and 10,000 parts by weight of Mannitol;

between 10 and 500 parts by weight of stearic acid;

between 10 and 500 parts by weight of Titanium Dioxide;

According to a preferred embodiment of the invention the water content of the excipients is very low. More specifically the water content in the diluents is very low in order to minimize the water content of the pharmaceutical composition. Lactose is used in its anhydrous form.

Furthermore, all excipients may be applied in a dry form.

In accordance with a second aspect, the subject-matter of the present invention is a pharmaceutical preparation, in the form of tablet or powder, characterised in that it contains a composition as defined previously associated if required with at least one customary additive selected from among the sweeteners, flavouring agents, colours and lubricants.

The choice of these additives and their quantity can easily be determined by a person skilled in the art.

Another manufacturing process for pharmaceutical compositions according to the invention is mixing of 5-[[4-[3-Methyl-4-oxo-3,4-dihydro-2-quinazolinyl]methoxy]phenyl-methyl]thiadiazolidine-2,4-dione, one or more antioxidants and other pharmaceutical excipients followed by melt granulation in a high shear mixer. Hydrogenated, vegetable oil, waxes or other low temperature melting binders can be used. The granules can be filled into capsules, compressed into tablets or used in other pharmaceutical dosage forms.

More preferably the manufacturing process applied is direct compression of tablets, wherein 5-[[4-[3-Methyl-4-oxo-3,4-dihydro-2-quinazolinyl]methoxy]phenyl-methyl]thiadiazolidine-2,4-dione, one or more antioxidants and other excipients suitable for direct compression are mixed followed by tabletting.

Yet, another preferred embodiment of the manufacturing process is wet granulation, where granules are obtained by wet massing of 5-[[4-[3-Methyl-4-oxo-3,4-dihydro-2-quinazolinyl]methoxy]phenyl-methyl]thiadiazolidine-2,4-dione, together with one or more anti-oxidants and other excipients.

It is assumed that the contact time with water have to be very short.

The most preferred process comprises the direct compression whereby 5-[[4-[3-Methyl-4-oxo-3,4-dihydro-2-quinazolinyl]methoxy]phenyl-methyl]thiadiazolidine-2,4-dione is kept at conditions of low water vapour pressure.

A sweetener may be a natural sugar such as sorbitol or a synthetic product such as saccharine or aspartame.

When the antioxidant selected is ascorbylpalmitat, propylgallat, which is a powder, it can be advantageous to mix it in an appropriate excipient such as α-tocopherol succinat, lactose or cellulose micrycristalline.

The present invention will further be illustrated with the following non-exhaustive examples.

In Example 1 through 4 the tablets were prepared according to the following procedure:

The active ingredient is mixed with cellulose microcrystalline in a drum mixer for 10 minutes. Lactose is added and the mixing continued for further two minutes.

The lubricants are added and the mixing continued for further two minutes.

EXAMPLE 1

25 mg 5-[[4-[3-methyl-4-oxo-3,4-dihydro-2-quinazolinyl]methoxy]phenyl-methyl]thiadiazolidine-2,4-dione, potassium salt Tablets 807227

| | |
|---|---|
| 5-[[4-[3-methyl-4-oxo-3,4-dihydro-2-quinazolinyl]methoxy]phenyl-methyl]thiadiazolidine-2,4-dione, potassium salt, 003/97 | 9% |
| Cellulose Microcrystalline | 20% |
| Lactose | 66% |
| Magnesium Stearate | 0.5% |
| Talc | 4.5% |

EXAMPLE 2

50 mg 5-[[4-[3-methyl-4-oxo-3,4-dihydro-2-quinazolinyl]methoxy]phenyl-methyl]thiadiazolidine-2,4-dione, potassium salt tablets 807237

| | |
|---|---|
| 5-[[4-[3-methyl-4-oxo-3,4-dihydro-2-quinazolinyl]methoxy]phenyl-methyl]thiadiazolidine-2,4-dione, potassium salt, 003/97 | 18% |
| Cellulose Microcrystalline | 20% |
| Mannitol | 57% |
| Magnesium Stearate | 0.5% |
| Talc | 4.5% |

EXAMPLE 3

50 mg 5-[[4-[3-Methyl-4-oxo-3,4-dihydro-2-quinazolinyl]methoxy]phenyl-methyl]thiadiazolidine-2,4-dione, potassium salt Tablets 731725

| | |
|---|---|
| 5-[[4-[3-methyl-4-oxo-3,4-dihydro-2-quinazolinyl]methoxy]phenyl-methyl]thiadiazolidine-2,4-dione, potassium salt | 18% |
| Lactose | 81.5% |
| Magnesium stearate | 0.5% |

EXAMPLE 4

0.25 mg 5-[[4-[3-methyl-4-oxo-3,4-dihydro-2-quinazolinyl]methoxy]phenyl-methyl]thiadiazolidine-2,4-dione, potassium salt Tablets 728625

| | |
|---|---|
| 5-[[4-[3-methyl-4-oxo-3,4-dihydro-2-quinazolinyl]methoxy]phenyl-methyl]thiadiazolidine-2,4-dione, potassium salt | 0.09% |
| Mannitol | 98% |
| Magnesium stearate | 2% |

EXAMPLE 5

| | |
|---|---|
| 5-[[4-[3-methyl-4-oxo-3,4-dihydro-2-quinazolinyl]methoxy]phenyl-methyl]thiadiazolidine-2,4-dione, potassium salt | 0.09% |

| | |
|---|---|
| Hydrogenated vegetable oil | 6.25% |
| Talc | 5% |
| α-tocopherol | 50% of 5-[[4-[3-methyl-4-oxo-3,4-dihydro-2-quinazolinyl]methoxy]phenyl-methyl]thiadiazolidine-2,4-dione, potassium salt |
| Lactose DCL21/Mannitol | Up to 200 g |

The granulate is manufactured in a Baker Perkins 1 L high-shear mixer—using a water bath of 70° C. The mixing is carried out at 3000 RPM, chopper 6000 RPM and the granulation is performed at approx. 70° C. The hot granulate is sieved through sieve 1.25 μm, and the cold granulate through sieve 1000 μm. The glidant is added with a card for 2 min. The tablets are manufactured using a Diaf tablet machine with 9 mm punch.

In order to protect against light and improve the appearance of the tablets, the tablets are film-coated.

The tablets were coated with the following film-coating composition where an amount of coating material of 5 mg/cm$^2$ were chosen as being satisfactory with respect to stability of the tablets:

| | |
|---|---|
| Methylhydroxypropylcellulose, Ph. Eur. | ~4.34 mg/tablet |
| Titanium Dioxide, Ph. Eur. | ~1.73 — |
| Purified Water, Ph. Eur. | q.s. — |

Talc, Ph. Eur. (Added as polishing agent at the end of the film-coating process (0.5% w/w of tablet core). Absorbed amount is not quantified.

EXAMPLE 6

| | |
|---|---|
| 5-[[4-[3-methyl-4-oxo-3,4-dihydro-2-quinazolinyl]methoxy]phenyl-methyl]thiadiazolidine-2,4-dione, potassium salt | 0.09% |
| Povidone | 7.5% |
| Hydroxypropylmethyl cellulose | 1.5% |
| Croscarmelose sodium | 1.56% |
| Talc | 1.1% |
| Magnesium stearate | 0.5% |
| Lactose 300 mesh | up to 200 g |

The granulate is manufactured by Baker Perkins 1 L intensive mixer. Dry mixing were carried out at 500 RPM, chopper 1500 RPM and granulation 1000 RPM and 2000 RPM. The wet granulate is sieved through sieve 1.25 μm and the dry granulate through sieve 1000 μm. The glidant is admixed with a card for 2 min. The tablets are manufactured by Diaf tablet machine with 9 mm punch.

EXAMPLE 7

Composition: Oral Powder, 1 mg/ml, 100 ml

| | |
|---|---|
| 5-[[4-[3-Methyl-4-oxo-3,4-dihydro-2-quinazolinyl]methoxy]phenyl-methyl]thiadiazolidine-2,4-dione potassium salt | 0.1096 g |
| Mannitol | 2.5 g |
| Hydroxypropyl-β-cyclodextrin | 10 g |

To be diluted with 92 mL water before use.

EXAMPLE 8

Composition: Oral Powder, 10 mg/ml, 100 ml

| | |
|---|---|
| 5-[[4-[3-Methyl-4-oxo-3,4-dihydro-2-quinazolinyl]methoxy]phenyl-methyl]thiadiazolidine-2,4-dione potassium salt | 1.096 g |
| Mannitol | 2.5 g |
| Hydroxypropyl-β-cyclodextrin | 10 g |
| Sodium Carbonate, anhydrous, Na$_2$CO$_3$ | 15 mg |

To be diluted with 92 mL water before use.

The invention claimed is:

1. A tablet formed by direct compression of a composition that consists essentially of 5-[[4-[3-methyl-4-oxo-3,4-dihydro-2-quinazolinyl]methoxy]phenyl-methyl]thiazolidine-2,4-dione or a pharmaceutically acceptable salt thereof, and pharmaceutically acceptable excipients, said excipients consisting essentially of between 100 and 400,000 parts by weight of anhydrous lactose, between 111 and 10,000 parts by weight of microcrystalline cellulose, expressed in parts by weight per 100 parts of 5-[[4-[3-methyl-4-oxo-3,4-dihydro-2-quinazolinyl]methoxy]phenyl-methyl]thiazolidine-2,4-dione or one of its pharmaceutically acceptable salts, magnesium stearate and talc, wherein magnesium stearate constitutes between 2.78 and 500 parts by weight of the tablet, expressed in parts by weight per 100 parts of 5-[[4-[3-methyl-4-oxo-3,4-dihydro-2-quinazolinyl]methoxy]phenyl-methyl]thiazolidine-2,4-dione or one of its pharmaceutically acceptable salts, and wherein the excipients have a water content below about 1%.

2. The tablet according to claim 1, wherein the excipients are in a dry form.

* * * * *